United States Patent [19]

Opalko

[11] 4,358,452
[45] Nov. 9, 1982

[54] N-[1,2,3,4,6,7,12,12
α-OCTAHYDRO-2H-INDOLO(2,3α)-
QUINOLIZINYL-2β-YL]ALKANE AND
BENZYL SULFONAMIDES AND
ANTI-HYPERTENSIVE USE THEREOF

[75] Inventor: Albert Opalko, Maidenhead, England

[73] Assignee: John Wyeth & Brother Limited, Maidenhead, England

[21] Appl. No.: 253,975

[22] Filed: Apr. 13, 1981

[30] Foreign Application Priority Data

May 9, 1980 [GB] United Kingdom ............... 8015474

[51] Int. Cl.³ ................ A61K 31/445; C07D 471/04
[52] U.S. Cl. ................................. 424/256; 546/70
[58] Field of Search ...................... 546/70; 424/256

[56] References Cited

U.S. PATENT DOCUMENTS 4,052,404 10/1977 Szantay et al. ................. 546/70
4,181,657 1/1980 Havera et al. .................. 546/70

FOREIGN PATENT DOCUMENTS 1435573 5/1976 United Kingdom .

OTHER PUBLICATIONS

Klioze et al., J. Med. Chem., 1979, 22, pp. 1497–1504.

Primary Examiner—David B. Springer
Attorney, Agent, or Firm—Richard K. Jackson

[57] ABSTRACT

Indoloquinolizines of the formula (I)

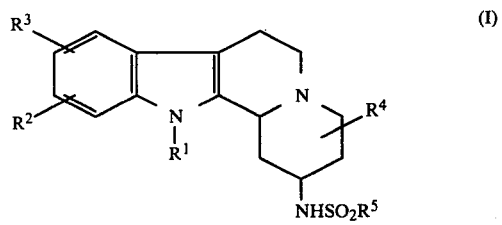

and their pharmaceutically acceptable acid addition salts [wherein $R^1$ represents hydrogen, lower alkyl or lower aralkyl, $R^2$ and $R^3$ each represent hydrogen, halogen, lower alkoxy or lower alkyl, $R^4$ represents hydrogen, halogen or lower alkyl and $R^5$ represents lower alkyl or aryl] possess antihypertensive activity.

5 Claims, No Drawings

N-[1,2,3,4,6,7,12,12a-OCTAHYDRO-2H-INDOLO(2,3a)-QUINOLIZINYL-2β-YL]ALKANE AND BENZYL SULFONAMIDES AND ANTI-HYPERTENSIVE USE THEREOF

The invention relates to novel indole derivatives, more particularly to novel indoloquinolizines, to processes for preparing the compounds, to their use and to pharmaceutical compositions containing them.

The present invention provides novel indoloquinolizines of the general formula (I)

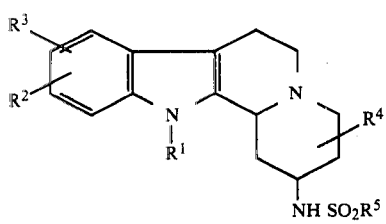

and the pharmaceutically acceptable acid addition salts thereof, wherein $R^1$ represents hydrogen, lower alkyl or lower aralkyl, $R^2$ and $R^3$ each represent hydrogen, halogen, lower alkoxy or lower alkyl, $R^4$ represents hydrogen, halogen or lower alkyl and $R^5$ represents lower alkyl or aryl.

The terms "lower alkyl" and "lower alkoxy" as used herein indicate that the alkyl and alkoxy radicals each contain from 1 to 6 carbon atoms. Those radicals containing from 1 to 4 carbon atoms are preferred. The term "lower aralkyl" indicates that the radical contains from 7 to 10, preferably 7 to 9, carbon atoms. When a radical is referred to as "aryl" or part of a radical is "aryl" as in "aralkyl" the aryl group is preferably a phenyl or substituted phenyl group. The substituted phenyl group can be a phenyl group substituted by one or more substituents chosen from, for example, halogen (e.g. chlorine, fluorine or bromine), lower alkoxy (e.g. methoxy or ethoxy), lower alkyl (e.g. methyl, ethyl, propyl or butyl), alkylenedioxy (e.g. methylenedioxy or ethylenedioxy), amino, lower alkylamino, diloweralkylamino or trifluoromethyl.

Examples of the group $R^1$ are hydrogen, methyl, ethyl, propyl, butyl, benzyl and p-chlorobenzyl. Preferably $R^1$ is hydrogen or methyl. Examples of $R^2$ and $R^3$ are hydrogen, halogen such as fluorine, chlorine or bromine, lower alkoxy such as methoxy, ethoxy, propoxy or butoxy and lower alkyl such as methyl, ethyl, propyl or butyl. Preferably both $R^2$ and $R^3$ are hydrogen. Examples of $R^4$ are hydrogen, halogen such as fluorine, chlorine or bromine and lower alkyl such as methyl, ethyl, propyl or butyl. Preferably $R^4$ is hydrogen. $R^5$ can be lower alkyl (e.g. methyl, ethyl, propyl or butyl) or aryl (e.g. phenyl or substituted phenyl as mentioned above). Preferably $R^5$ is lower alkyl such as methyl.

The compounds of the invention can be prepared by a process in which an amine of general formula (II)

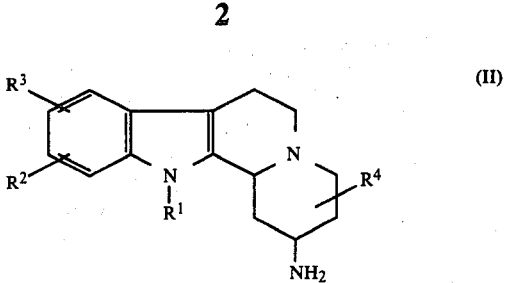

(where $R^1$, $R^2$, $R^3$ and $R^4$ have the meanings given above) or an acid addition salt thereof, is reacted with a reactive derivative of a sulphonic acid compound of formula (III)

$$R^5SO_2OH \qquad (III)$$

As a reactive derivative of the sulphonic acid it is preferable to use an acid halide (for example the chloride or bromide) or an anhydride. The reaction may be carried out under basic conditions. The amine of formula (II) and the reactive derivatives of the acid of formula (III) are known compounds or they can be prepared by methods known in the art for preparing analogous compounds. For example, amines of formula (II) are disclosed in U.K. patent specification No. 1,435,573.

An alternative method of preparing the novel compounds of the invention comprises cyclising an N-oxide of general formula (IV)

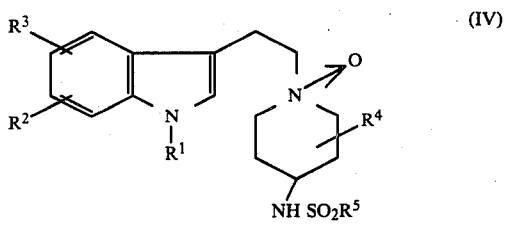

where $R^1$, $R^2$, $R^3$, $R^4$ and $R^5$ are as defined hereinabove. The cyclisation of compounds of general formula (IV) may be brought about in a number of ways. For example a compound of formula (IV) may be cyclised by heating in the presence of ferrous ions and a suitable acidic medium. Examples of suitable acidic media are methanol/acetic acid or sulphuric acid/pyridine. Examples of compounds giving ferrous ions are ferrous sulphate and ferrous chloride. Alternatively cyclisation of compounds of general formula (IV) may be accomplished by reaction with trifluoroacetic anhydride/H+ mixtures, e.g. a mixture of trifluoroacetic anhydride and trifluoroacetic acid. The starting material of general formula (IV) may be prepared by N-oxidising a compound of general formula (V)

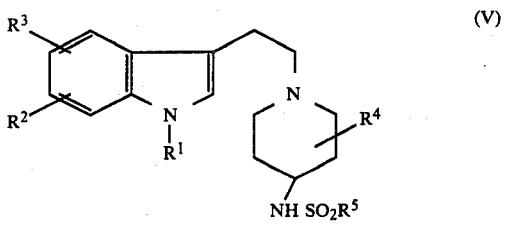

where $R^1$, $R^2$, $R^3$, $R^4$ and $R^5$ are as defined above. The N-oxidisation may be effected with an N-oxidising agent e.g. hydrogen peroxide or a peroxy acid (e.g. m-chloroperbenzoic acid).

If necessary in the reactions hereinbefore described, reactive substituent groups may be protected during a reaction and the protecting group removed at a later stage. Once the compound of general formula (I) has been prepared then if necessary a substituent in the molecule may be converted into another substituent specified in connection with general formula (I).

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of the invention possess at least two asymmetric carbon atoms and hence they can exist in various stereochemical forms. In addition they can exist as cis or trans isomers. It will be realised that if, for example, the starting material of formula (II) is a mixture of isomers the product of formula (I) will also be a mixture of isomers which can be separated, if required, by standard procedures. The preferred compounds of the invention are the trans isomers in which the —NH SO$_2$R$^5$ group is in the equatorial position i.e. compounds of the general formula (VI)

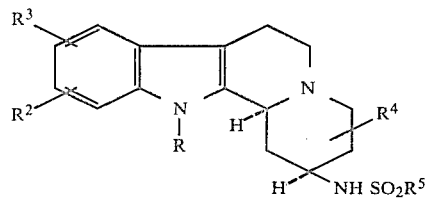

(VI)

and the pharmaceutically acceptable acid addition salts thereof (wherein R$^1$, R$^2$, R$^3$, R$^4$ and R$^5$ are as defined above). These compounds can be prepared by the methods described above e.g. starting from the corresponding trans isomer of general formula (II).

The compounds of the invention have pharmacological activity. For example, the compounds exhibit antihypertensive activity upon administration to warm-blooded animals according to a standard pharmacological procedure. One such pharmacological test procedure is described below:

Female rats are rendered hypertensive by implanting subcutaneously two wax pellets (30 mg) containing desoxycorticosterone acetate (15 mg) followed immediately by uninephrectomy. The drinking water is replaced by normal saline ad lib for 4 weeks. Blood pressure stabilises at a hypertensive level after 6 weeks. Systolic pressure is measured indirectly before dosing with a test compound using an E and M pneumatic pulse transducer and a Devices MX2 recorder. Groups of 4 rats are dosed orally with suspensions or solution of the test compound in 0.5% hydroxypropylmethylcellulose 0.9% saline vehicle. Blood pressures are recorded again at 2,6 and 24 hours and the results, expressed as a percentage of the pre-dose values compared with those of a similar group of rats receiving vehicle alone.

In the aforementioned test N-[1,2,3,4,6,7,12,12bα-octahydro-2H-indolo[2,3-a]quinolizin-2β-yl]methanesulphonamide, a representative compound of the present invention, was found to lower blood pressure by 51.7% 2 hours after dosing and by 46.2% 6 hours after dosing when administered at 50 mg/kg.

The invention further provides a pharmaceutical composition comprising a compound of general formula (I) or a pharmaceutically acceptable salt thereof in association with a pharmaceutically acceptable carrier. Any suitable carrier known in the art can be used to prepare the pharmaceutical composition. In such a composition, the carrier is generally a solid or liquid, or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweetners, flavouring agents, suspending agents, thickening agents, colours, viscosity regulators, stabilisers, or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glyceroland glycols) and their derivatives, and oils (e.g. fractionated coconut oil and arachis oil). For parental administration the carrier can also be an oily ester such as ethyl oleate and isopropyl myristate. Sterile liquid carriers are used in sterile liquid form compositions for parental administration. The liquid carrier for pressurised compositions can be a halogenated hydrocarbon or other pharmaceutically acceptable propellant.

Liquid pharmaceutical compositions which are sterile solutions or suspensions can be utilised by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example packeted powders, vials, ampoules, prefilled syringes or sachets containing liquids. The unit dosage form can be for example, a capsule or tablet itself, or it can be the appropriate number of any such compositions, in package form. The quantity of the active ingredient in a unit dose of composition may be varied or adjusted from 0.5 mg. or less to 750 mg. or more, according to the particular need and the activity of the active ingredient. The invention also includes the compounds in the absence of the carrier where the compounds are in unit dosage form.

The following Examples illustrate the invention

EXAMPLE 1

N-[1,2,3,4,6,7,12,12bα-Octahydro-2H-indolo[2,3-a]quinolizin-2β-yl]methanesulphonamide A solution of 2β-amino-1,2,3,4,6,7,12,12bα-octahydro-2H-indolo[2,3-a]quinolizine (4.87 g; 20.18 mM) and triethylamine (2.1 g; 20.3 mM) in dichloromethane (50 cm³) was stirred at 0° (ice) as a solution of methanesulphonic anhydride (3.51 g; 20.17 mM) in dichloromethane (25 cm³) was added slowly. The clear solution was then warmed to room temperature and allowed to stand over the weekend (70 h). The mixture was washed with water (2×50 cm³) and dried (MgSO4). Filtration and evaporation afforded a dark glass (5.28 g) which was purified by chromatography on silica and eluted with 10% ethanol in ethyl acetate, to give the title compound as a yellow solid (2.77 g). The base was converted to the hydrochloride giving the hydrochloride quarterhydrate (2.30 g) as cream-yellow needles, m.p. 247°–253° (dec) (with signs of decomposition at temperatures above 220°).

A sample (0.25 g) of the hydrochloride was converted to the base with aqueous bicarbonate and dichloromethane. Crystallisation from ethanol gave the free base quarterhydrate (0.13 g) as cream cubes, m.p. 250°–255° (dec). Found: C,59.28%; H,7.00%;N,12.82% $C_{16}H_{21}N_3O_2S.\frac{1}{4}H_2O$ requires C, 59.32%; H,6.69%; N, 12.97%.

The NMR and IR spectra confirmed the 2β and 12bα stereochemistry.

EXAMPLES 2 TO 4

By procedures analogous to that of Example 1 the following compounds are prepared:

| Example | Product |
| --- | --- |
| 2 | N—[1,2,3,4,6,7,12,12b-octahydro-2H—indolo[2,3-a]quinolizin-2-yl]ethanesulphonamide |
| 3 | N—[1,2,3,4,6,7,12,12b-octahydro-2H—indolo[2,3-a]quinolizin-2-yl]benzenesulphonamide |
| 4 | N—[12-ethyl-1,2,3,4,6,7,12,12b-octahydro-2H indolo[2,3-a]quinolizin-2-yl]methane- |

-continued

| Example | Product |
| --- | --- |
| | sulphonamide |

I claim:

1. A compound of the formula:

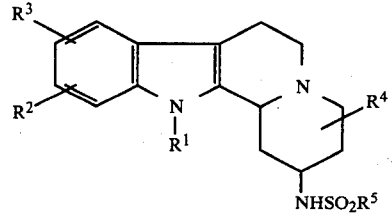

in which
$R^1$ is hydrogen, alkyl of 1 to 6 carbon atoms or aralkyl of 7 to 10 carbon atoms;

$R^2$ and $R^3$, independently, are hydrogen, halogen, alkoxy of 1 to 6 carbon atoms or alkyl of 1 to 6 carbon atoms with the proviso that when $R^2$ and $R^3$ are tertiary alkyl groups they are on nonadjacent carbon atoms;

$R^4$ is hydrogen, halogen or alkyl of 1 to 6 carbon atoms;

$R^5$ is alkyl of 1 to 6 carbon atoms, phenyl or substituted phenyl in which the substituent is halogen, alkoxy of 1 to 6 carbon atoms, alkyl of 1 to 6 carbon atoms, alkylenedioxy of 1 to 6 carbon atoms, amino, alkylamino of 1 to 6 carbon atoms, dialkylamino of 2 to 12 carbon atoms or trifluoromethyl; or a pharmaceutically acceptable acid addition salt thereof.

2. A compound as claimed in claim 1 wherein $R^1$ is hydrogen, methyl, ethyl, propyl, butyl, benzyl or p-chlorobenzyl, $R^2$, $R^3$ are each hydrogen and $R^5$ is lower alkyl.

3. A compound as claimed in claim 1 which is N-[1,2,3,4,6,7,12,12bα-octahydro-2H-indolo[2,3-a]quinolizin-2β-yl]methanesulphonamide or a pharmaceutically acceptable acid addition salt thereof.

4. A pharmaceutical composition having antihypertensive activity comprising a compound selected from the group consisting of an indoloquinolizine of the formula:

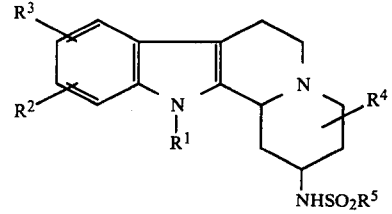

or a pharmaceutically acceptable acid addition salt thereof, wherein $R^1$ is hydrogen, alkyl of 1 to 6 carbon atoms or aralkyl of 7 to 10 carbon atoms;

$R^2$ and $R^3$, independently, are hydrogen, halogen, alkoxy of 1 to 6 carbon atoms or alkyl of 1 to 6 carbon atoms with the proviso that when $R^2$ and $R^3$ are tertiary alkyl groups they are on nonadjacent carbon atoms;

R[4] is hydrogen, halogen or alkyl of 1 to 6 carbon atoms;

R[5] is alkyl of 1 to 6 carbon atoms, phenyl or substituted phenyl in which the substituent is halogen, alkoxy of 1 to 6 carbon atoms, alkyl of 1 to 6 carbon atoms, alkylenedioxy of 1 to 6 carbon atoms, amino, alkylamino of 1 to 6 carbon atoms, dialkylamino of 2 to 12 carbon atoms or trifluoromethyl; and a pharmaceutically acceptable carrier.

5. A method of treating hypertension in a mammal which comprises administering to said mammal an antihypertensively effective amount of a compound selected from the group consisting of an indoloquinolizine of the formula

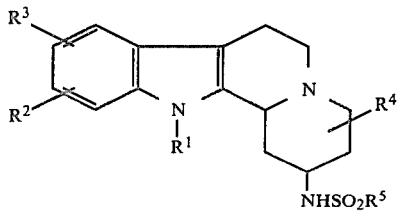

or a pharmaceutically acceptable acid addition salt thereof, wherein

R[1] is hydrogen, alkyl of 1 to 6 carbon atoms or aralkyl of 7 to 10 carbon atoms;

R[2] and R[3], independently, are hydrogen, halogen, alkoxy of 1 to 6 carbon atoms or alkyl of 1 to 6 carbon atoms with the proviso that when R[2] and R[3] are tertiary alkyl groups they are on nonadjacent carbon atoms;

R[4] is hydrogen, halogen or alkyl of 1 to 6 carbon atoms;

R[5] is alkyl of 1 to 6 carbon atoms, phenyl or substituted phenyl in which the substituent is halogen, alkoxy of 1 to 6 carbon atoms, alkyl of 1 to 6 carbon atoms, alkylenedioxy of 1 to 6 carbon atoms, amino, alkylamino of 1 to 6 carbon atoms, dialkylamino of 2 to 12 carbon atoms or trifluoromethyl.

* * * * *